United States Patent [19]

Ohno et al.

[11] 4,273,944
[45] Jun. 16, 1981

[54] METHOD FOR SELECTIVE PREPARATION OF CIS ISOMERS OF ETHYLENICALLY UNSATURATED COMPOUNDS

[75] Inventors: Shigeru Ohno, Kanagawa; Haruya Tezuka, Omiya; Toshinobu Ishihara, Niigata, all of Japan

[73] Assignee: Shin-Etsu Chemical Co., Ltd., Tokyo, Japan

[21] Appl. No.: 89,466

[22] Filed: Oct. 30, 1979

[30] Foreign Application Priority Data

Nov. 8, 1978 [JP] Japan ................................. 53-137543

[51] Int. Cl.$^3$ ..................... C07C 5/09; C07C 45/62; C07C 29/17
[52] U.S. Cl. .................................. 568/396; 568/350; 568/318; 568/459; 568/420; 568/434; 568/903; 568/857; 568/816; 568/799; 562/512; 562/400; 562/405; 585/500; 585/350; 585/435; 252/473; 252/474
[58] Field of Search ..................... 260/593 R; 568/903, 568/816, 799, 396, 350, 318, 459, 420, 435, 857; 585/500, 350, 435; 252/473, 474; 562/512, 400, 405

[56] References Cited

U.S. PATENT DOCUMENTS

| | | | |
|---|---|---|---|
| 2,681,938 | 6/1954 | Lindlar | 252/473 |
| 3,522,192 | 7/1970 | Maxwell | 252/473 |
| 4,009,126 | 2/1977 | McFarland | 252/473 |

FOREIGN PATENT DOCUMENTS

3512762 of 0000 Japan.
3623317 of 0000 Japan.
3864875 of 0000 Japan.

OTHER PUBLICATIONS

Ozer et al., Chem. Abst., vol. 85, #63190n (1976).
Kinoshito et al., Chem. Abst., vol. 87, #52747q (1977).
Borunova et al., Chem. Abst., vol. 82, #3088f (1975).
Nikitin et al., Chem. Abst., vol. 57, #16371e.
Aerov et al., Chem. Abst., vol. 85, #159382c (1976).

*Primary Examiner*—Natalie Trousof
*Assistant Examiner*—James H. Reamer
*Attorney, Agent, or Firm*—Toren, McGeady and Stanger

[57] ABSTRACT

A novel method for the selective preparation of the cis isomer of a disubstituted ethylenically unsaturated compound is proposed in which a disubstituted acetylenically unsaturated compound is partially hydrogenated in the presence of, in place of a conventional Lindlar catalyst or a combination of a Lindlar catalyst with an amine, a palladium catalyst borne on an alumina carrier in combination with water and a hydroxide or a basic salt of an alkali metal or an alkaline earth metal. The inventive method is advantageous over conventional methods by the unnecessity of the use of an amine compound which is definitely undesirable when the product is directed to the application in perfumery and by the easiness in handling of the catalyst which can be easily separated from the reaction mixture after completion of the reaction.

6 Claims, No Drawings

METHOD FOR SELECTIVE PREPARATION OF CIS ISOMERS OF ETHYLENICALLY UNSATURATED COMPOUNDS

BACKGROUND OF THE INVENTION

The present invention relates to a method for the preparation of cis isomers of ethylenically unsaturated compounds or, more particularly, to a method for the selective preparation of cis isomers of ethylenically unsaturated organic compounds by the partial hydrogenation of corresponding acetylenically unsaturated compounds.

As is well known, various kinds of cis isomers of ethylenically unsaturated compounds are very important in the fields of perfumery, agricultural chemicals, medicines and the like and an important method for the preparation thereof is the partial hydrogenation of the triple bond in acetylenically unsaturated compounds into double bond.

Such a selective partial hydrogenation can be performed only by use of a suitable catalyst and one of the most widely used catalysts for the purpose is the so-called Lindlar catalyst which is a palladium catalyst borne on a calcium carbonate carrier and partially poisoned or inactivated with lead. Further, an improvement in the selectivity of the hydrogenation with the Lindlar catalyst up to a practical level has been proposed in which the Lindlar catalyst is used in combination with an amine compound such as quinolines, hexamethylenetetramine, a lower alkylamine and the like (see, for example, Japanese Patent Publications Nos. 35-12762, 36-23317 and 38-64875). One of the problems in the combined use of such amine compounds is the contamination of the product compound with the amine compound used in the hydrogenation reaction so that the use of an amine compound with unpleasant odor is absolutely unsuitable, especially, when the cis isomer as the hydrogenation product is to be directed to the application in perfumery in which any smallest amount of such a contamination is fatal for the quality of the product.

Another problem inherent to the Lindlar catalyst is in the separation and recovery of the catalyst after completion of the hydrogenation reaction. Since the Lindlar catalyst is borne on a calcium carbonate carrier, the catalyst is likely comminuted in the course of the reaction into very finely divided powder so that the separation of the catalyst from the reaction mixture can be performed only with an extreme difficulty. Distillation of the reaction mixture containing the catalyst unremoved in a fine powdered form, even if the amount is very small, is sometimes undesirable, especially, when the product is directed to the perfumery use because of the possible deleterious effects on the quality of the perfume product.

Thus, it has long been desired to develop a novel catalyst for the partial hydrogenation of a disubstituted acetylenic compound into corresponding ethylenically unsaturated compound, in particular, in the form of the cis isomer, which can give high selectivity and reactivity in the reaction and high quality of the products suitable for use even in perfumery as well as easiness in handling thereof.

SUMMARY OF THE INVENTION

It is therefore an object of the present invention to provide a novel method for the selective preparation of cis isomers of ethylenically unsaturated compounds by the partial hydrogenation of the corresponding acetylenically unsaturated compounds free from the above described problems in the prior art methods.

The inventive method for the selective preparation of cis isomers of ethylenically unsaturated compound by the partial hydrogenation of disubstituted acetylenic compounds comprises pressurizing the disubstituted acetylenic compound with hydrogen in the presence of a partially inactivated palladium catalyst borne on an alumina carrier, water and a hydroxide or a basic salt of a metal selected from the group consisting of alkali metals and alkaline earth metals.

DETAILED DESCRIPTION OF THE PREFERRED EMBODIMENTS

The starting material used in the inventive method is a disubstituted acetylenic compound represented by the general formula $R^1C\equiv CR^2$, where $R^1$ and $R^2$ are each a hydrocarbon group having no triple bond such as alkyl groups, cycloalkyl groups, alkenyl groups and aryl groups and those groups derived from the above named hydrocarbon groups by replacing one or more of the hydrogen atoms therein with hydroxy groups, carboxyl groups, aldehyde groups or carbonyl oxygen atoms. In most cases, the groups $R^1$ and $R^2$ each have from 1 to 20 carbon atoms.

Several of the examples of the acetylenic compounds in which one or both of the groups $R^1$ and $R^2$ are the substituted hydrocarbon groups as mentioned above with one or more of hydroxy groups or carbonyl oxygen atoms are: 3-hexyn-1-ol, dehydrojasmone, 7-eicosyn-11-one, 1-phenyl-2-pentyn-1-ol, 2-propyn-1-ol, butyn-2-diol-1,4, 6-heneicosyn-11-one and the like.

The inventive method utilizes specifically a palladium catalyst borne on an alumina carrier in an amount from 3 to 15% by weight of palladium based on the total amount of the catalyst. When the amount of palladium is smaller than 3% by weight, the selectivity for the cis isomer is decreased with increased formation of the saturated compound and decreased yield of the objective cis isomer while excessive amounts of palladium over 15% by weight may result in coming off of the palladium from the carrier to a great economical disadvantage by the loss of expensive palladium.

The palladium catalyst must also be partially poisoned or inactivated with a poisoning element selected from the group consisting of zinc, lead and tin in an amount from 0.5 to 10% by weight based on the total amount of palladium and the alumina carrier. Smaller amounts of the poisoning element than 0.5% by weight result in an increased yield of the saturated compounds while excessive amounts of the poisoning element over 10% by weight sometimes lead to a decreased velocity of the hydrogenation reaction to an impractical extent.

The amount of the above described catalyst to be used in the inventive method is preferably in the range from 0.05 to 5% by weight based on the amount of the disubstituted acetylenic compound as the starting material since smaller amounts of the catalyst than 0.05% by weight cannot give a sufficiently high velocity of the reaction while larger amounts of the catalyst than 5% by weight are undesirable due to the decreased selectivity for the formation of the objective cis isomer.

In the next place, the palladium catalyst as described above must be used in the inventive method in combination with two kinds of promotors, viz, water and a compound of an alkali metal or an alkaline earth metal. The amount of water in the reaction mixture is preferably in the range from 0.1 to 10% by weight based on the amount of the disubstituted acetylenic compound as the starting material since smaller amounts of water than 0.1% by weight result in an insufficient yield of the objective cis isomer while larger amounts of water than 10% by weight are also undesirable due to the decrease in the yield.

The second promoter in the catalyst system is a hydroxide or a basic salt of an alkali metal or an alkaline earth metal, i.e. lithium, sodium, potassium, magnesium, calcium, strontium or barium. The basic salts of these elements are exemplified by the carbonates, hydrogen carbonates and acetates. The amount of the hydroxide or a basic salt of the metallic element is preferably in the range from 0.05 to 10% by weight based on the amount of the disubstituted acetylenic compound as the starting material since smaller amounts of the compound than 0.05% by weight lead to an increased formation of the saturated compounds with decreased selectivity for the formation of the objective cis isomers while larger amounts of the compound than 10% by weight sometimes bring about polymerization of the starting material and/or the reaction product or formation of unidentified compounds with unpleasant odor.

The reaction of the inventive method is carried out at a temperature preferably in the range from 20° to 200° C. When the reaction is carried out at a temperature lower than 20° C., the reaction velocity is markedly decreased with lower selectivity for the formation of the objective cis isomer while a reaction carried out at a temperature higher than 200° C. will result in an increased yield of the saturated compound giving a product of inferior quality.

The pressure in the reaction vessel which is produced by pressurizing with hydrogen is preferably in the range from 1 to 100 kg/cm$^2$G though not particularly limitative. When the pressure is lower than 1 kg/cm$^2$G, the reaction velocity is decreased with a lower selectivity for the formation of the objective cis isomer while a pressure higher than 100 kg/cm$^2$G is undesirable due to the increased yield of the saturated compound with, consequently, a lower quality of the final product.

Following are the examples to illustrate the inventive method in further detail but not to limit the scope of the invention in any way.

EXAMPLE 1

Into an autoclave of 200 ml capacity were introduced 50 g of 7-eicosyn-11-one, 0.1 g of a palladium catalyst containing 10% by weight of palladium on an alumina carrier and partially inactivated with 1.7% by weight of zinc and 0.2 g of an aqueous solution containing 20% by weight of a sodium hydroxide and the vessel was pressurized with hydrogen gas up to a pressure of 5 kg/cm$^2$G followed by agitation of the reaction mixture at 50° C., upon which absorption of hydrogen took place at a rate of 0.1 liter per minute. The pressure was maintained at 5 kg/cm$^2$G by further supply of hydrogen in compensation for the consumed volume. When the absorption of hydrogen ceased after 42 minutes, the agitation was stopped and the reaction mixture was kept standing for 5 minutes during which the catalyst powder settled completely in the reaction mixture. After separation of the reaction mixture and the catalyst by filtration, the filtrate was subjected to distillation to give a liquid product which was identified by gas chromatography to be the desired cis-7-eicosen-11-one. The yields of the above cis compound, the corresponding trans isomer and the saturated compound were 97.0%, 2.7% and 0.3%, respectively.

EXAMPLE 2

Into an autoclave of 1 liter capacity were introduced 500 g of 3-hexyn-1-ol, 0.5 g of a palladium catalyst containing 10% by weight of palladium borne on an alumina carrier and partially inactivated with 1.7% by weight of zinc, 0.5 g of anhydrous sodium carbonate and 1 g of water and the reaction vessel was pressurized with hydrogen gas up to a pressure of 5 kg/cm$^2$G. The reaction mixture was agitated at 50° C. while maintaining the above pressure, whereupon absorption of hydrogen took place at a rate of about 1 liter per minute. When the absorption of hydrogen ceased after 125 minutes, the agitation was stopped and the reaction mixture was kept standing for 5 minutes to settle the catalyst powder completely in the reaction mixture. After removal of the catalyst by filtration, the reaction mixture was subjected to distillation to give a liquid product which was identified by gas chromatographic analysis to be mainly cis-3-hexen-1-ol. The yields of this cis compound, the corresponding trans compound and the corresponding saturated compound were 98.2%, 1.6% and 0.18%, respectively.

EXAMPLE 3

The same experimental procedure as in Example 1 was repeated except that the catalyst system was composed of the same amount of the same palladium catalyst in combination with 0.1 g of barium hydroxide and 1.0 g of water. The absorption of hydrogen ceased after 46 minutes from the beginning of agitation. The yields of cis-7-eicosen-11-one, the corresponding trans compound and the corresponding saturated compound were 97.8%, 2.0% and 0.23%, respectively.

COMPARATIVE EXAMPLE 1

The same experimental procedure as in Example 2 was repeated except for the omission of anhydrous sodium carbonate and water. The results of the gas chromatographic analysis of the reaction mixture indicated that the yields of cis-3-hexen-1-ol, the corresponding trans compound and the corresponding saturated compound were 86.1%, 13.2% and 0.70%, respectively.

COMPARATIVE EXAMPLE 2

The experimental procedure was the same as in Example 2 except that the content of palladium in the catalyst was 1% by weight instead of 10% by weight. The results of the gas chromatographic analysis of the reaction mixture indicated that the yields of cis-3-hexen-1-ol, the corresponding trans compound and the corresponding saturated compound were 84.2%, 13.4% and 2.39%, respectively.

COMPARATIVE EXAMPLE 3

The experimental procedure was exactly the same as in Example 2 except that the carrier of the palladium catalyst was calcium carbonate instead of alumina. Separation of the catalyst from the reaction mixture after completion of the reaction was carried out with difficulty. The results of the gas chromatographic analysis of the reaction mixture indicated that the yields of cis-3-hexen-1-ol, the corresponding trans compound and the corresponding saturated compound were 84.8%, 13.5% and 1.65%, respectively.

EXAMPLE 4

Into an autoclave of 1 liter capacity were introduced 500 g of 3-hexyn-1-ol, 0.5 g of a catalyst containing 5% by weight of palladium borne on an alumina carrier and partially inactivated with 3% by weight of lead, 0.5 g of anhydrous sodium carbonate and 1.0 g of water and the hydrogenation reaction was carried out substantially in the same manner as in Example 2. The gas chromatographic analysis of the reaction mixture indicated that the yields of the objective cis-3-hexen-1-ol, the corresponding trans compound and the corresponding saturated compound were 97.5%, 2.2% and 0.3%, respectively.

EXAMPLE 5

Into an autoclave of 1 liter capacity were introduced 500 g of 3-hexyn-1-ol, 0.5 g of a catalyst containing 5% by weight of palladium borne on an alumina carrier and partially inactivated with 3% by weight of tin, 0.5 g of anhydrous sodium carbonate and 1.0 g of water and the hydrogenation reaction was carried out substantially in the same manner as in Example 2.

The gas chromatographic analysis of the reaction mixture indicated that the yields of the objective cis-3-hexen-1-ol, the corresponding trans compound and the corresponding saturated compound were 97.0%, 2.5% and 0.5%, respectively.

What is claimed is:

1. A method for the selective preparation of the cis isomer of a disubstituted ethylenically unsaturated compound by the partial hydrogenation of a disubstituted acetylenically unsaturated compound which comprises pressurizing a disubstituted acetylenically unsaturated compound having the formula $$R^1C\equiv CR^2$$

wherein $R^1$ and $R^2$ contain from 1 to 20 carbon atoms and are each a hydrocarbon radical selected from the group consisting of alkyl, cycloalkyl, alkenyl and aryl, each of which may be substituted with hydroxy, carboxyl, aldehyde, or carbonyl with hydrogen in the presence of a catalyst containing from 3% to 15% by weight of palladium borne on an alumina carrier and partially inactivated with a poisoning element selected from the group consisting of zinc, lead and tin, water and a hydroxide or a basic salt selected from the group consisting of carbonate, hydrogen carbonate or acetate of a metallic element selected from the group consisting of alkali metals and alkaline earth metals and wherein the reaction of partial hydrogenation is carried out at a temperature in the range from 20° to 200° C. and under a hydrogen pressure in the range from 1 to 100 kg/cm$^2$G.

2. The method as claimed in claim 1 wherein the amount of the poisoning element for the partial inactivation of the palladium catalyst is in the range from 0.5% to 10% by weight based on the amount of the catalyst.

3. The method as claimed in claim 1 wherein the amount of water is in the range from 0.1% to 10% by weight based on the amount of the disubstituted acetylenically unsaturated compound.

4. The method as claimed in claim 1 wherein the amount of the hydroxide or the basic salt is in the range from 0.05% to 10% by weight based on the amount of the disubstituted acetylenically unsaturated compound.

5. The method as claimed in claim 1 wherein the amount of the catalyst is in the range from 0.05% to 5% by weight based on the amount of the disubstituted acetylenically unsaturated compound.

6. The method of claim 1 wherein the disubstituted acetylenically unsaturated compound is selected from the group consisting of 3-hexyn-1-ol, dehydrojasmone, 7-eicosyn-11-one, 1-phenyl-2-pentyn-1-ol, 2-propyn-1-ol, butyn-2-diol-1,4, and 6-heneicosyn-11-one.

* * * * *